United States Patent [19]

Ugolini

[11] Patent Number: 4,923,472

[45] Date of Patent: May 8, 1990

[54] ARTIFICIAL KNEE-JOINT

[75] Inventor: Filippo Ugolini, Rome, Italy

[73] Assignee: Salus S.r.l., Rome, Italy

[21] Appl. No.: 298,616

[22] Filed: Jan. 18, 1989

[30] Foreign Application Priority Data

Jan. 22, 1988 [IT] Italy ................. 47565 A/88

[51] Int. Cl.⁵ ............................. A61F 2/38
[52] U.S. Cl. ..................... 623/20; 623/18; 623/38
[58] Field of Search ........... 623/20, 18, 16, 21, 623/38, 39

[56] References Cited

U.S. PATENT DOCUMENTS

| | | | |
|---|---|---|---|
| 3,824,630 | 7/1974 | Johnston | 623/20 |
| 3,918,101 | 11/1975 | Lagrange et al. | 623/20 |
| 4,112,522 | 9/1978 | Dadurian et al. | 623/20 X |
| 4,301,553 | 11/1981 | Noiles | 623/20 |
| 4,375,703 | 3/1983 | Evans et al. | 623/21 |
| 4,462,120 | 7/1984 | Rambert et al. | 623/20 |
| 4,578,081 | 3/1986 | Harder et al. | 623/20 X |

FOREIGN PATENT DOCUMENTS

| | | | |
|---|---|---|---|
| 2839093 | 3/1980 | Fed. Rep. of Germany | 623/20 |
| 2502937 | 10/1982 | France | 623/20 |
| 532377 | 10/1976 | U.S.S.R. | 623/20 |

Primary Examiner—Ronald L. Frinks
Attorney, Agent, or Firm—Beveridge, DeGrandi & Weilacher

[57] ABSTRACT

An artificial knee joint includes two hinge members connected together by a bearing, and detachable dovetail couplings which connect the hinge members to rods that are inserted respectively in the bony cavities of the femoral and tibial bones.

12 Claims, 3 Drawing Sheets

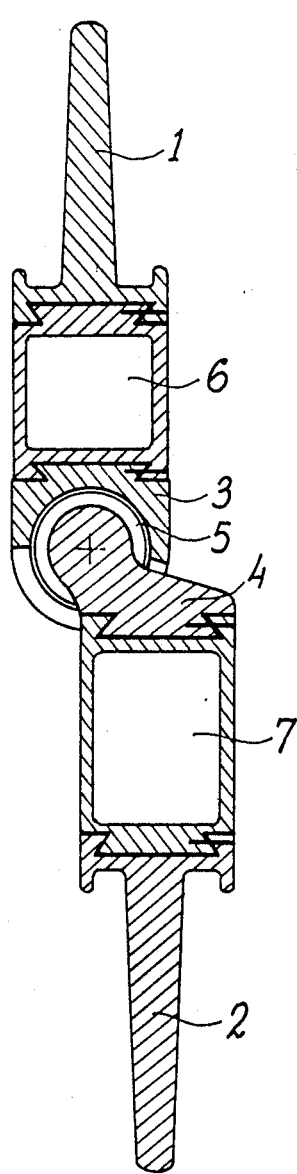
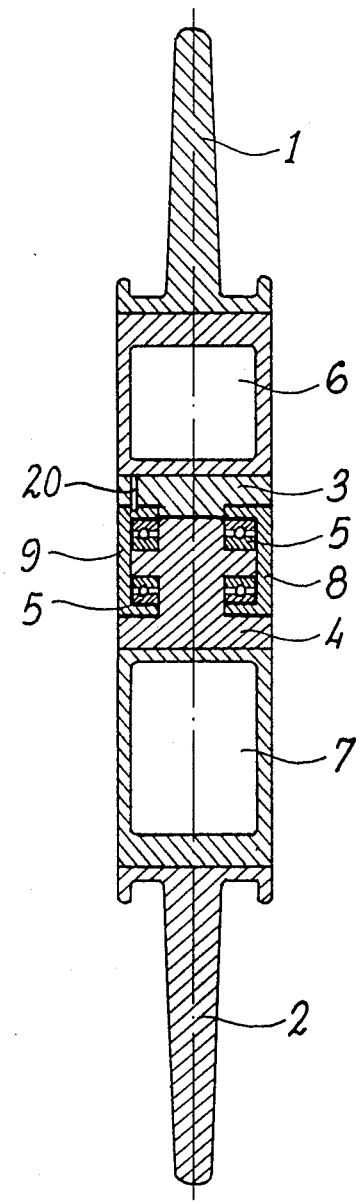
Fig. 1                    Fig. 2

ARTIFICIAL KNEE-JOINT

BACKGROUND OF THE INVENTION

This invention relates to an artificial articulation. More particularly this invention relates to a knee-joint suitable to replace the natural knee-joint. The artificial knee joint is connected rigidly to the femoral bone and to the tibial bone and it allows an optimal reproduction to be obtained of motions of the natural knee-joint.

As is well known, a correct deambulation in all situations such as climbing or descending the stairs or the like, or merely walking, is permitted by the presence of such a delicate and complex knee-joint articulation.

When the knee-joint is no longer able to perform its original task because of various reasons, it is necessary to replace the knee-joint by means of a surgical operation.

Prostheses available and commonly employed at the present time are not always suitable to reproduce the functionality of the natural articulation satisfactorily, in particular because friction occurring in the mechanical device makes the correct deambulation motion toilsome.

Moreover, prostheses available at present almost always require some surgical adaptations of the prostheses themselves.

Indeed, prostheses available up to now are mounted in situ by assembling the hinge during the surgical operation. The functions of the rods, spacers and the hinge itself are integrated with each other, with little or no possibility of adjusting the size to fit the particular requirements that may be found during the operation. The actual size required may be different from the size foreseen before the operation, for example, at the time of diagnosis and designing of the artificial joint.

SUMMARY OF THE INVENTION

In light of the practical difficulties stemming from the employment of prostheses already known, and in order to obviate their drawbacks, the applicant has devised an improved artificial knee-joint. This artificial knee-joint is mechanically and functionally structured as to allow an articulation to be construction which is equivalent to that obtained with the natural articulation. The individual parts of the artificial joint are constructed in a modular way in order to provide the most suitable prostheses by sizes and types for the actual surgical requirements. These requirements are determinable during the operation itself.

Moreover, the artificial articulation proposed according to the invention is not affected by significant frictional forces between its mechanical parts, so that no difficulties arise in the deambulation motions.

It is a further object of the present invention to provide an artificial articulation whose position can be suitably adjusted independently of the way the femoral and tibial bones of the patient have been amputated.

The solution proposed by the inventor provides an articulation which is rigidly connected to the femoral and to the tibial bones so as to allow a hinge bending to be obtained of the two parts through an arc of about 120°, possibly with a small negative angle.

These results are obtained by providing an artificial articulation which is made up of two hinge members coupled by means of two rolling bearings and integrally fastened, respectively, to the femoral bone and to the tibial bone. Some spacing members may be interposed for restoring the original length of the leg, if necessary.

Accordingly, the present invention relates to an artificial articulation, more particularly a knee-joint, comprising a first rod insertable into the cavity of the femoral bone; a first hinge member connected to said first rod, at its end opposite to that which is inserted into the bony cavity; a second rod, insertable into the bony cavity of the tibial bone; a second hinge member connected to said second rod, at its end opposite to that which is inserted into the bony cavity. The articulated coupling between said two hinge members is obtained through at least one bearing. Said two hinge members can be shaped so that the vertical axis of the first rod—first hinge member assembly and the vertical axis of the second rod—second hinge member assembly are parallel to the second rod shifted forward with respect to the first one, in the direction of step.

The two rods are inserted, cemented or uncemented, in the respective bony cavities, or fixed by means of screws. The rods are shaped and/or knurled to obtain an easy and durable coupling with the bone.

The coupling between each rod and the respective hinge member can be fixed or it can be removable.

In the latter instance, at least one spacing member can be provided between the rod and the hinge member, such spacer being of variable height depending on the requirements at hand, and allowing the articulation to be positioned correctly according to the extent of surgical ablation.

Mechanical means are provided for coupling the rod to the spacing member or to the hinge member or viceversa, said means comprising a locking sleeve for the two coupled ends, or of a joint, as for instance a dovetail joint, with mechanical locking means.

Alternatively, some spacing shims can be arranged on each rod instead of said spacing members.

Said mechanical locking means can be made up of a dowel which possibly is threaded and self-locking, or, in the case of members of cylindrical shape, such means can comprise a selflocking threaded collar or an elastic ring.

Bearings employed for the coupling between the two hinge members are preferably of the self-lubricating rolling type and two are supplied.

In order to allow the bearings or other mechanical components to be replaced, the coupling between the two hinge members can also be constructed so that it is removable and is locked by cover means which are assembled on said bearings and fastened to their positions by pin means or the like.

BRIEF DESCRIPTION OF THE DRAWINGS

This invention will be disclosed in the following just for illustrative and not for limitative purposes with particular reference to the figures of the enclosed drawings, wherein:

FIG. 1 is a cross-sectional side view of a particular embodiment of the articulation according to the present invention;

FIG. 2 is a cross-sectional front view of the articulation of FIG. 1;

DETAILED DESCRIPTION OF THE PREFERRED EMBODIMENTS

Figure 3:
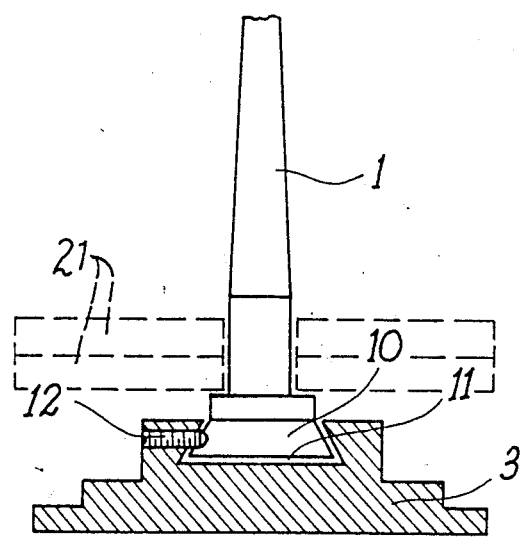
FIG. 3 is a front view of a first embodiment of the fastening system between the rod and the spacer or the hinge of the articulation.

With reference now to FIGS. 1 and 2, the numeral 1 points out the femoral rod which will be inserted into the central bony cavity of the femoral bone. The numeral 2 points out the tibial rod that will be inserted into the central bony cavity of the tibial bone.

The hinge member which is integral with the rod 1 is pointed out by the reference numeral 3, whereas the rod 2 is integrally coupled to the hinge member 4.

The two hinge members 3 and 4 are connected to rotate with respect to one another through the interposition of the rolling bearings 5.

According to the specific cases at hand, the spacers 6 and 7 can be provided between the rod 1 and the hinge member 3, and between the rod 2 and the hinge member 4.

The coupling between the rod 1 or 2 and the spacer 6 or 7 and between the spacer 6 or 7 and the hinge member 3 or 4 is obtained through dovetail joints which will be illustrated below with reference to FIGS. 3-7.

To allow the surgeon to perform a convenient mounting of the prosthesis, the two assemblies consisting of (i) rod 1, optional spacer 6 and hinge 3, and (ii) rod 2, optional spacer 7 and hinge 4, can be mounted separately. Then two assemblies can be coupled and connected functionally by means of the two covers 8 and 9 which are kept locked by pins 20.

This configuration makes it possible to remove the covers 8,9 and replace one of the rolling bearings or both of them, in case of necessity, or to replace any other component parts.

As can be observed in particular in FIG. 1, the axis of the rod 1—spacer 6—hinge 3 assembly and the axis of the rod—2 spacer 7—hinge 4 assembly are parallel but they are out of alignment. The second axis is shifted forward with respect to the first one, in the direction of the patient's step, so that an absolute stability of the system is obtained when the full body weight is lying on the articulation.

FIGS. 3-7 show various couplings between the rod 1 or 2 and the spacer 6 or 7 or the hinge member 3 or 4. It is evident that the articulation according to the present invention can also be constructed without the insertion of any spacers, by making the rod 1 and the hinge members 3 and the rod 2 and the hinge member 4 integral with each other. As shown in broken lines in FIG. 3, shims 21 can be arranged on each rod.

The disclosure of the FIGS. 3-7 is given with reference to the coupling between the rod 1 or 2 and the hinge members 3 or 4, but it is to be understood that the same coupling can be made between the spacer 6 or 7 and the rod 1 or 2 or the hinge member 3 or 4.

Figure 4:
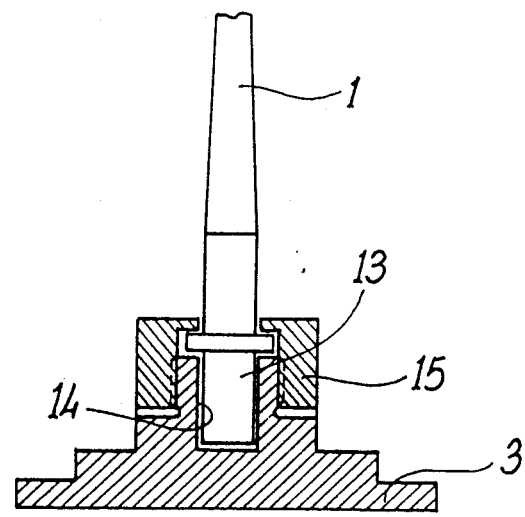
FIG. 4 is a front view of a second embodiment of the fastening system between the rod and the spacer or the hinge of the articulation.

FIG. 3 shows a coupling with a mechanical guide comprising a dovetail joint 10 - 11 which is locked by the locking dowel 12, while the coupling shown in FIG. 4 is obtained through the insertion of the end 13 of the rod 1 into the cavity 14 in the hinge member 3, which is locked by the sleeve 15.

Figure 5:
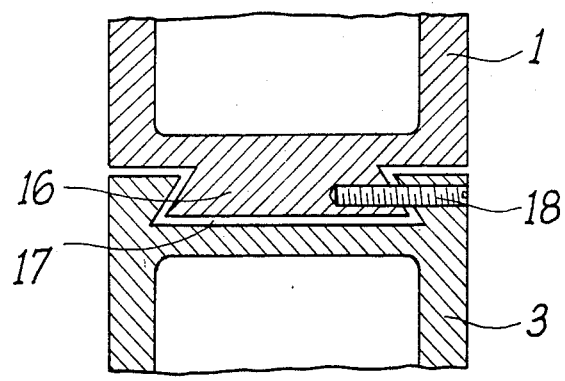
FIG. 5 is a front view of a third embodiment of the fastening system between the rod and the spacer or the hinge of the articulation.
Figure 6:
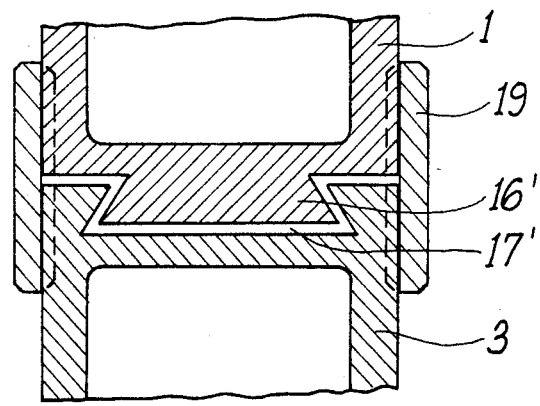
FIG. 6 is a front view of a further embodiment of the fastening system between the rod and the spacer or the hinge of the articulation.

The dovetail joint (male member 16 - female member 17) shown in FIG. 5 is locked by a self-locking threaded dowel 18, whereas the similar coupling (members 16' and 17') illustrated in FIG. 6 is locked through the employment of a threaded collar 19. Such a coupling can only be employed in the case of cylindrical joints.

Figure 7:
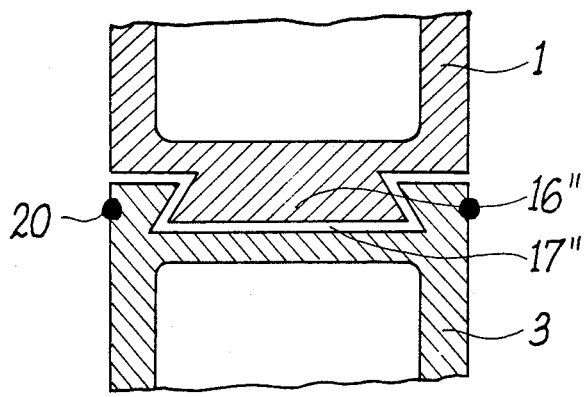
FIG. 7 is a front view of a fifth embodiment of the fastening system between the rod and the spacer or the hinge of the articulation.

The elastic ring 20 employed for locking the members 16" and 17" of FIG. 7 can also be advantageously employed.

Employing such type of solutions to the problem, the spacers 6 and 7 being provided optionally, it is possible to replace completely the proper articulation without removing the rods 1 and 2, in the very rare cases when this is necessary.

The present invention has been disclosed just for illustrative and not for limitative purposes according to some preferred embodiments of the same, but it is to be understood that modifications and/or changes can be made by those who are skilled in the art without departing from the spirit and scope of the invention.

I claim:

1. An artificial articulation, in particular an artificial knee-joint, comprising, a first rod insertable into the bony cavity of the femoral bone; a first hinge member connected to an end of said first rod that is opposite to its end that is inserted into the bony cavity of the femoral bone; a second rod insertable into the bony cavity of the tibial bone; a second hinge member connected to an end of said second rod that is opposite to its end that is inserted into the bony cavity of the tibial bone; characterized in that a coupling between each said rod and its respective hinge member is of the removable type and includes a mechanical means made up of a dove-tail shaped male-female type joint, and in that an articulated coupling between said two hinge members is provided by at least one bearing.

2. An artificial articulation according to claim 1, characterized in that a spacing member is provided between said rods and their respective hinge members.

3. An artificial articulation according to claim 1, characterized in that said bearings are self-lubricating bearings of the rolling type.

4. An artificial articulation according to claim 1 or 3 characterized in that two said bearings are provided.

5. An artificial articulation according to claim 1 or 2, characterized in that a locking means is provided for mechanically locking said coupling.

6. An artificial articulation according to claim 5, characterized in that said locking means includes a dowel.

7. An artificial articulation according to claim 6, characterized in that said dowel is of the self-locking threaded type.

8. An artificial articulation according to claim 5, characterized in that said locking means includes a selflocking threaded collar.

9. An artificial articulation according to claim 5, characterized in that said locking means includes an elastic ring.

10. An artificial articulation according to any one of claims 1, 2 or 3, characterized in that the two hinge members are shaped so that the vertical axis of the first rod and the vertical axis of the second rod, but the axis of the second rod is shifted forward with respect to the first axis in the direction of the patient's step.

11. An artificial articulation according to claim 1, characterized in that spacing shims are provided on said rods.

12. An artificial articulation according to claim 5 wherein the locking means includes covers which are assembled laterally on said bearings and kept fastened by pin means.

* * * * *